United States Patent [19]

Hagfors et al.

[11] 4,237,899

[45] Dec. 9, 1980

[54] ELECTRONIC TISSUE STIMULATOR WITH OUTPUT SIGNAL CONTROLS

[75] Inventors: Norman R. Hagfors, Fridley, Minn.; John W. Keller, Jr., Miami, Fla.

[73] Assignee: Stimtech, Inc., Minneapolis, Minn.

[21] Appl. No.: 945,975

[22] Filed: Sep. 26, 1978

[51] Int. Cl.³ ............................................. A61N 1/36
[52] U.S. Cl. .................................................. 128/422
[58] Field of Search ........ 128/419 E, 419 PG, 419 R, 128/420, 421, 422, 423

[56] References Cited

U.S. PATENT DOCUMENTS

| | | | |
|---|---|---|---|
| 2,771,554 | 11/1956 | Gratzl | 128/421 |
| 3,589,370 | 6/1971 | McDonald | 128/421 |
| 3,888,261 | 6/1975 | Maurer | 128/421 |
| 3,946,745 | 3/1976 | Hsiang-Lai et al. | 128/421 |
| 3,989,051 | 11/1976 | Nozhnikov et al. | 128/421 |

FOREIGN PATENT DOCUMENTS 972199 6/1959 Fed. Rep. of Germany ........... 128/422
1055776 10/1953 France ..................................... 128/422

Primary Examiner—William E. Kamm
Attorney, Agent, or Firm—Audley A. Ciamporcero, Jr.

[57] ABSTRACT

In a transcutaneous nerve stimulating apparatus, the stimulating pulse wave form is shaped and manipulated to accommodate specific physiological parameters, and to allow multiple non-interfering electrode administrations. The stimulating pulse wave form, of desired pulse rate, pulse duration, and pulse amplitude, optionally includes successive pulses of alternating plurality, which may all be coupled to a single electrode, alternately coupled to plural electrodes, or the like. Pulse decay is controlled, as is pulse rise time. Voltage regulation is provided to the pulse generation apparatus.

5 Claims, 4 Drawing Figures

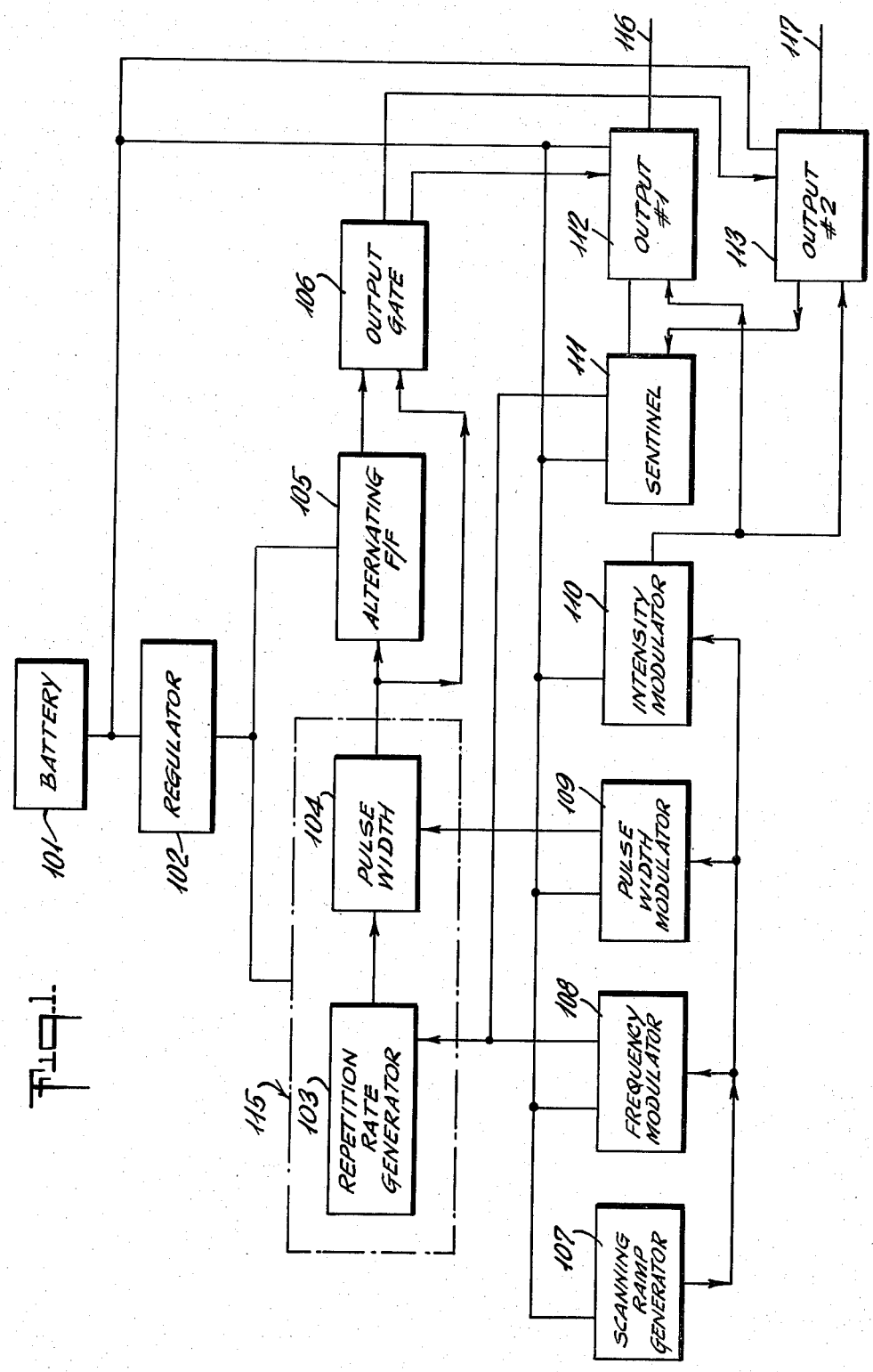

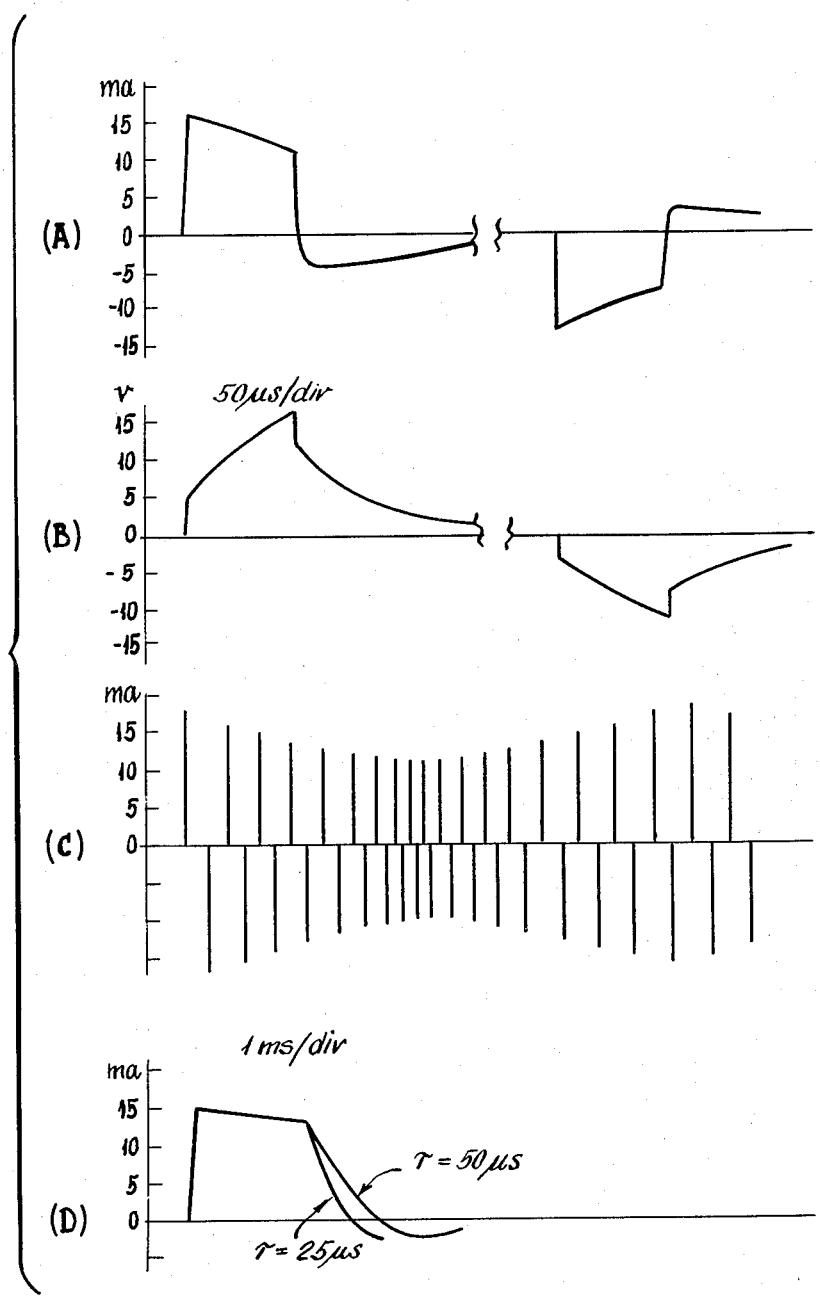

ELECTRONIC TISSUE STIMULATOR WITH OUTPUT SIGNAL CONTROLS

TECHNICAL BACKGROUND

This invention relates to body function stimulating apparatus, and more particularly to apparatus and methods for controlling pain through the use of transcutaneous electrical nerve stimulation. Still more particularly, it relates to nerve stimulation apparatus and methods wherein the stimulating signals or pulses are characterized by specified wave shapes and wave characteristics, including alternating pulses and controlled pulse rise and pulse decay times.

BACKGROUND ART

There is a long history of the employment of electrical shocks for various therapeutic needs. Centuries ago, electric eels were employed to provide the desired stimulation. Even to the present, some believe it to be beneficial to apply successive electrical shocks to the musculature, either to achieve muscular contractions, or for desired theremic action. See, for example, U.S. Pat. Nos. 2,936,762 and 3,261,358 to P. D. Bernard.

Electrical stimulation of human tissue has received its greatest acceptance in recent years with respect to electrical stimulation of the heart to force pumping action, and to maintain adequate blood flow through the system. Further, increasing sophistication in semi-conductor components and miniaturization thereof has allowed for corresponding sophistication in terms not only of the types of application of electrical stimulation, but furthermore to the ultimate controllability of the stimulating signals themselves. Present applications include stimulation of the carotid sinus, the urinary bladder, the intestines, the diaphragm, and the like. Further, there is ever increasing interest in the utilization of electrical stimulation of the nervous system to alleviate pain.

It is well known that living cells, both nerve and muscle cells, consist of an outer membrane containing an inner fluid of more or less structured water, containing various chemical ions such as potassium, calcium, and sodium. These ions are charged particles, and their concentration inside and outside the cells results in an electrical and chemical polarization between the inside and outside of the cell wall. Muscular contraction and nervous communication is carried on by a depolarization of these cells. It is also well known that depolarization of these cells can be initiated by artificial electrical stimulation.

Predictably, different types of cells generally require correspondingly different types of electrical stimulating signals. For example, even considering nerve cells, there are different strength and duration requirements for electrical pulses which will effectively stimulate sensor (Class A afferent), motor (efferent), and noxous (Class C nociceptor) cells. Generally, this results from the rather wide differences involved in the ranges of natural pulse repetition frequencies found in the various nerves. For example, the repetition frequency of the nervous signal stimulating the heart is of the order of 1 Hz, while the repetition frequency of pain provoked signals in the Class C fibers is on the order of 100 Hz.

There also exist differences in the parameters required for stimulation when a stimulating electrode is placed adjacent the cells that are being stimulated (e.g., the heart), as opposed to when the electrode placement is less proximate the cells being stimulated (e.g., electrodes at skin surface for stimulating a nerve several millimeters beneath the skin). Included among the critical output stimulation parameters are pulse repetition frequency, pulse duration, pulse amplitude, pulse polarity, and pulse shape or configuration. Additionally, the application schedule of stimulation will affect the clinical effectiveness thereof (e.g., stimulating for one hour, followed by two hours' rest, and so on).

Accordingly, selection of parameters of a given stimulator will be influenced by the particular type of stimulation sought. For example, it is generally held that very short pulses will be relatively more effective in stimulating small fibers than are relatively long pulses. Hence, when an electrode is placed within the proximity of more than one nerve in the same general area, and it is desired to stimulate one of them, some selectivity may be achieved by optimizing the stimulating parameters for that particular nerve. The field of optimization and selectivity is at this time, however, rather nascent.

In a co-pending application of W. Keller, concurrently filed herewith (STM-11), entitled "PROGRAMMABLE ELECTRONIC PAIN CONTROL WITH SCANNED OUTPUT PARAMETERS", there is set forth apparatus and methods whereby the important-stimulating signal parameters of pulse frequency, pulse duration, and pulse amplitude are respectively scanned through predetermined ranges of effective operation, whereby optimum stimulating criteria are achieved at least at a clinically acceptable frequency of occurrence.

A further complication with respect to the uniform administration of effective stimulation is the widespread diversity from person to person in physical nerve and muscle structure, and in associated electrical characteristics. These include not only the operational characteristics of the nerves, but also the locations of the nerves within the body and with respect to one another.

DISCLOSURE OF THE INVENTION

It is an object of the present invention to provide human body function stimulating apparatus which achieves relatively optimum effectiveness for a broad class of tissue or nerve types, and also accommodates a relatively broad range of variability in physiological structure of tissue and nerves.

It is a further object to provide such stimulating apparatus which is compatible for operation in conjunction with the scanning arrangements of the foregoing Keller concurrently filed co-pending application.

It is a still further object to provide stimulating apparatus which accommodates certain inherent operational characteristics of the nerves, including preferred responsiveness to particular polarities, and preferred recovery time characteristics after a stimulation pulse has been applied.

It is a further object to provide such apparatus which accommodates multiple electrode applications, in relative spatial proximity with one another, but without mutual interference which would detract from stimulation effectiveness.

It is a still further object to provide stimulating apparatus which retains effective stimulating signal characteristics notwithstanding a predetermined degree of degradation in the life or output power or voltage of a power source.

The present invention relates chiefly to the manipulation of the format and form of output signals from a tissue stimulator. That is, given the generation of a signal establishing the basic form of stimulation, designated a stimulation control signal, it is possible by further signal manipulation to enhance the effectiveness of the signal. In one aspect, successive stimulating signals have opposite polarities with respect to one another, thereby accommodating either a dual output electrode scheme, or likewise allowing for selective stimulation from the same electrode receiving pulses of both polarities. In another aspect, varying nerve thresholds are accommodated by tailoring of the pulses, for example shaping the pulse rise time, and more preferably, shaping the pulse decay in terms of time and rate of change. Such functions are compatible with one another, and additionally are compatible to the pulse rate scanning, pulse width scanning, and pulse amplitude scanning as described and claimed in the aforementioned concurrently filed co-pending application of Keller. Finally, all such features are compatible with a voltage regulating scheme, whereby a voltage regulation circuit operates under battery power, but delivers a relatively constant control voltage to the stimulation signal generating apparatus, notwithstanding aging and deterioration of the battery output characteristics.

It is a feature of the present invention that programmability of the various stimulation parameters is further enhanced, and the achievement of respective clinically acceptable results is rendered more likely.

BRIEF DESCRIPTION OF THE DRAWINGS

FIG. 1 shows a block diagrammatic version of an illustrative embodiment of the present invention;

FIG. 3 shows illustrative wave forms A through D with respect to the embodiments of FIGS. 1, 2A, and 2B.

BEST MODE FOR CARRYING OUT THE INVENTION

Figure 2A:
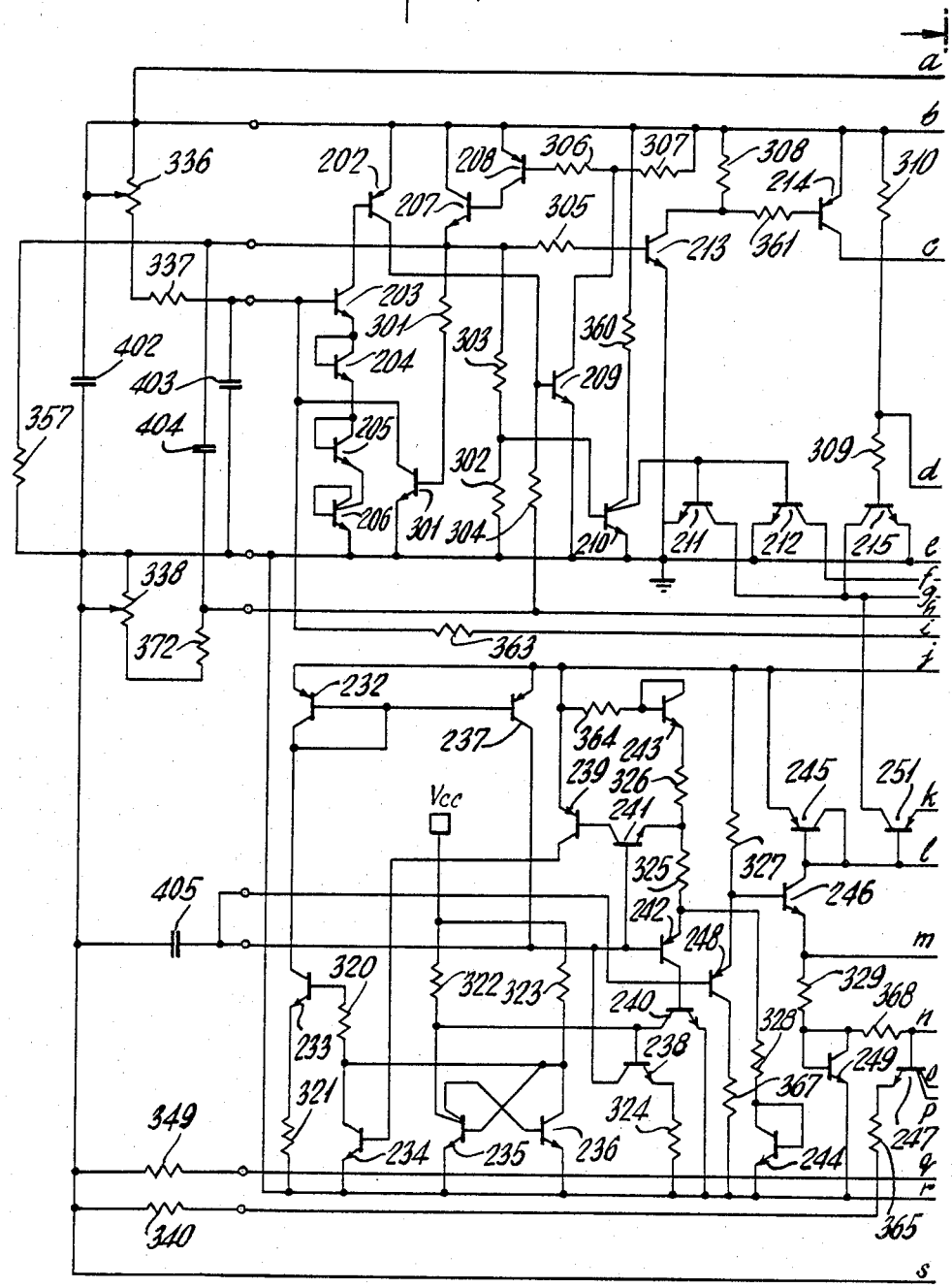
FIGS. 2A and 2B, when appropriately joined as shown, show a circuit schematic of a preferred embodiment of the present invention.

Referring first to FIG. 1, there is shown a block diagram of a transcutaneous nerve stimulation unit which embodies the principles of the present invention. It is noted that the embodiment of FIG. 1 includes not only the features and functions claimed herein in accordance with the principles of the present invention, but also features and functions common to the aforementioned concurrently filed co-pending application of Keller, and other desirable, real world features and functions of transcutaneous tissue stimulators. Essentially, the functional blocks of the embodiment of FIG. 1 may be regarded as being of five categories. These are: generation of power, at battery 101 and voltage regulator 102; generation of a stimulation control signal, defining the basic form and format of the signal, including oscillator 115, flip-flop 105, and gates 106, the scanning features, relating to continuous variation of critical signal parameters, including generator 107 and modulators 108, 109, and 110; output stages for generating the actual stimulation signal and coupling it to output terminals 116 and 117, including output unit number 1, 112 and output unit number 2, 113; and a so-called "sentinel" or protective feature at 111, for disabling the unit in the event of difficulty relating to electrode detachment or the like.

The embodiment of FIG. 1 operates as follows. The battery 101 provides a designated output voltage, which is coupled to a voltage regulator 102 and to the output, or power stages 112 and 113. The regulator 102 empowers the operation of the more critical signal generating portions such as oscillator 115 and flip-flop 105; that is, it is those elements for which constant signal production operation is desired even though the output of battery 101 may decay. Hence, the regulator 102 provides a substantially constant voltage to oscillator 115 and flip-flop 105 notwithstanding a predetermined amount of variation in the battery 101. The output stages 112 and 113, constituting power stages which require more substantial currents, are coupled directly to the battery 101. As described in the co-pending Keller application, the scanning apparatus 107 through 110 and the sentinel unit 111 are also powered from the battery. A scanning ramp generator 107 produces a ramp type signal which operates a frequency modulator 108, a pulse width modulator 109, and an intensity modulator 110, each of which produces a respective control signal in response to the varying amplitude from the ramp generator 107. The frequency modulator 108 controls the output rate of a repetition rate generator 103 aspect of oscillator 115; the pulse width modulator 109 controls the pulse width aspect 104 of oscillator 115; and the intensity modulator 110 controls the output amplitude of stages 112 and 113. The sentinel unit 111 senses the output impedance at 112 and 113, as well as the time rate of change of signals seen at the output of terminals 116 and 117, thereby to evaluate whether a dangerous or potentially shocking situation is occurring by virtue of electrode detachment or the like. The sentinel unit 111, upon detecting such a condition, disables the oscillator 115, in turn causing a cessation of application of stimulation signals to the user.

The oscillator 115, as represented by its repetition rate generator aspect 103 and pulse width aspect 104, produces a pulse signal having a predetermined pulse width, pulse rate, and pulse amplitude. In the embodiment shown, these attributes are to be scanned through predetermined ranges, but it will be understood that in accordance with the principles of the present invention, they may be set at predetermined, desired fixed values, either by hard wiring, by exterior adjustment, or by automatic programmability features. In any event, the pulse signal produced by oscillator 115 may be deemed a stimulation control signal, to be processed at alternating flip-flop 105 and output gate 106 for production of output signals at 116 and 117 via output amplifier stages 112 and 113. Hence, in the embodiment of FIG. 1, it will be appreciated that an advantageous mode of operation calls for interleaving, or alternating, of respective successive pulses of opposite polarities, with the coupling of pulses of one given polarity to one of the outputs, such as 116, and the coupling of the alternate, interleaved pulses of the opposite polarity to the other output 117 via the second output amplifier 113. To this end, the alternating flip-flop 105 has a bistable output which is a function of the receipt of successive pulses from the oscillator 115. Each pulse from oscillator 115 causes the output state of the flip-flop 105 to be reversed. Simultaneously, the pulse signal from oscillator 115 is coupled to an output gate 106, which gates signals alternately to output units 112 and 113. When the alternating flip-flop 105 has a given state, such as a logical one, the output gate couples a corresponding pulse from the oscillator 115 to a given one of the output units, such as 112. Thereafter, as the output state of flip-flop 105 shifts to the opposite state, such as a logical zero, the output gate 106 will be forced to gate the next pulse from oscillator 115 to the other output unit, such as the second output unit 113. Simultaneously, a polarity reversal occurs, although it will be appreciated that this polarity reversal may be accomplished either directly at the output gate 106, or by virtue of arrangement of polarities at the output stages 112 and 113. In either event, there is produced at output terminal 116 a pulse signal having a given polarity with respect to a datum or intermediate terminal (not shown), whereas there is produced at the other output 117 an interleaved pulse signal having pulses of the opposite polarity with respect to the datum or indifferent terminal. It will also be evident that the output terminals 116 and 117 as shown may in fact include a terminal pair while the other output 117 may include a distinct terminal pair, whereas with equal facility a third, grounded or indifferent electrode may be suitably coupled to the body of the user, with respect to which the pulses would be applied at single electrodes connected respectively to single lines 116 and 117.

A feature of the present invention not evident, but quite compatible with the embodiment of FIG. 1 relates to the shaping of the individual pulses. That is, it has been found that pulses of particular shape, especially in terms of the pulse rise time and pulse decay time, may be more effective for purposes of stimulation than corresponding "square" pulses, even at the same pulse rate, pulse duration, and pulse intensity. To this end, in accordance with the principles of the present invention the individual pulses are shaped as desired, in order to have a particular, predetermined pulse rise time, or even more preferably, a particular pulse decay time. It will be evident that those of ordinary skill in the art may achieve this pulse shaping function either at the oscillator 115, at the output gate 106, or at the output stages 112 and 113.

Although the embodiment of FIG. 1 employs a dual output scheme 112 and 113, it is within the scope of the principles of the present invention to utilize but a single output, such as the first output unit 112, but retaining each of the advantageous features of the principles of the present invention, including alternation of polarity of successive output pulses, and shaping of the pulse rise time and pulse decay time.

These features and functions may perhaps be better understood upon consideration of FIG. 3, parts A through D thereof, which show exemplary tissue stimulating wave forms. Part A of FIG. 3 shows an illustrative composite current output wave form, such as are applied to the electrodes and including pulses of both polarities, whether they are both to be applied to a single output unit such as 112. The pulses could alternately be coupled to the separate output units 112 and 113. The current output wave form of FIG. 3 part A employs the alternating pulse polarity aspect of the present invention, but does not employ different or distinctive pulse rise or pulse decay shaping. Part B of FIG. 3 shows a corresponding output voltage wave form, the distinction between parts A and B of FIG. 3 occurring in view of the nonlinearity of the impedance of the tissue being stimulated. Part C of FIG. 3 shows a wave form, compressed along the abscissa, or time reference, of an interleaved pulse wave form, wherein output current amplitude and repetition frequency are being scanned, separately and respectively for the positive and negative pulses thereof. Hence, the positive pulses are scanned to a maximum amplitude between 18 milliamperes and 12 milliamperes, whereas the negative pulses are scanned between minus 16.5 milliamperes and minus 10 milliamperes. The frequency for each phase is being scanned between 100 Hz and 200 Hz, at a scanning periodicity of 5 to 10 seconds. Part D of FIG. 3 shows exemplary variation of the output current pulse decay time and shape for two superimposed pulses, the more rapid one of which involving a decay time constant of 25 microseconds, on an exponential basis, and the more extended of which involves a decay time constant of 50 microseconds, also on an exponential basis.

It will therefore be seen from the wave shapes of FIG. 3A that the present invention relates in pertinent part to production of pulses of alternating polarity, and variation of pulse rise and decay times, which are quite compatible with the advantageous features of frequency scanning, pulse width scanning, and pulse intensity scanning.

Figure 2B:
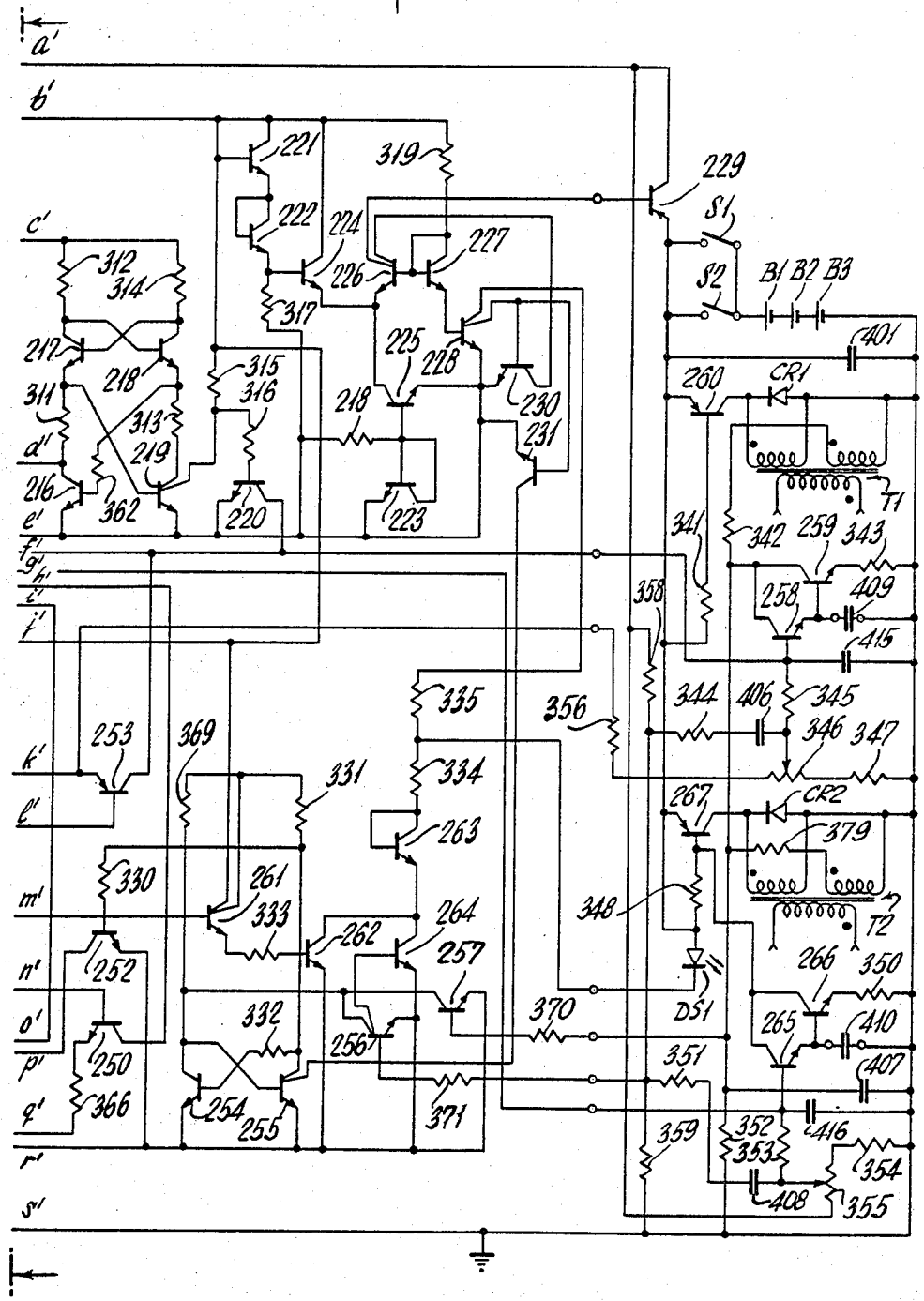

FIGS. 2A and 2B are to be connected at lines A—A′ through S—S′, respectively, to define a detailed circuit schematic of a preferred embodiment of the principles of the present invention, and more particularly a preferred configuration for the stimulator shown in block diagrammatic form in FIG. 1. It will be understood that the embodiment of FIGS. 2A and 2B represents an exemplary, practical total stimulator unit, including the features and functions claimed herein, those disclosed and claimed in the aforementioned concurrently filed application of Keller, and certain others which, although advantageous, are ancillary to the precepts of the principles of the present invention.

In FIG. 2B, batteries B1, B2, and B3 are series connected, and when switches S1 or S2 are closed, power is provided to the various circuitry. The unit of FIGS. 2A and 2B is a dual output unit, having respective output stages at transformers T1 and T2, with the secondaries of each transformer being connectable to suitable leads, in turn conveying the output stimulating pulses to electrodes disposed at appropriate places on the patient's body. Switch S1 is mechanically coupled to volume control potentiometer 346, as is Switch S2 with potentiometer 355. Further detail concerning the output stages is provided hereinafter.

The embodiment of FIGS. 2A and 2B includes a voltage regulator function, the apparatus for achieving such function being disposed at the upper rightmost section of FIG. 2B. A regulator transistor 229 has its emitter connected to the switches S1 and S2, and its base controlled by a differential amplifier formed by the emitter-base junction of transistors 226 and 224. The differential amplifier 226 and 224 senses the voltage attained by the difference between emitter-base voltage drops of transistors 221 and 222, off of the regulated voltage, $V_{CC}$, which is the voltage of the collector of regulating transistor 229, and the references provided by the base-emitter junction of transistor 228. Essentially, the voltage regulator function provides an independence of important system parameters from battery voltage, as the batteries age and the battery voltages decrease. Said otherwise, constant current output is achieved without the need for direct current regulation at the output.

The aspects of the embodiment of FIGS. 2A and 2B relating to the functions of oscillator 115 of FIG. 1 are located generally in the uppermost portion of FIG. 2A. That oscillator, which provides the essence of the output wave form in terms of pulse frequency and duration, is a free-running, multivibrator circuit, wherein transistors 207, 208, and 209 are "on" when an output pulse is being produced, and are "off" during the interval between output pulses. Pulse duration is established by the operation of capacitor 404 in conjunction with resistors 338 and 372. Output pulse repetition frequency is controlled by the capacitor 403 in conjunction with resistors 336 and 337.

The scanning oscillator which fulfills the function set forth with respect to scanning generator 107 of the FIG. 1 embodiment, is located at the lower leftmost portion of FIG. 2A. As described previously, the scanning ramp generator is an oscillator which provides a substantially lower frequency than that of the output of oscillator 115, the purpose of the scanning oscillator being to provide for parameter changes by scanning at a repetition frequency preferably measured in the range of seconds (whereas the repetition frequency of the main oscillator will normally be on the order of tens to hundreds per second). The scanning oscillator includes transistors 235 and 236 connected in a monostable multivibrator configuration. Whenever transistor 235 is conducting, transistor 233 is also conducting to provide a current to transistors 232 and 237, with transistor 237 being a current source to capacitor 405. Conversely, if transistor 236 is conducting, transistor 238 acts as a current sink to the same capacitor 405. Hence, whenever transistor 235 is conducting, the voltage on capacitor 405 is charging and changing positively, and when transistor 238 is conducting, the voltage on capacitor 405 is discharging and negative going. Transistor 241 determines the inflection point in the positive direction, and transistor 242 determines the inflection point in the negative direction. Accordingly, the voltage on capacitor 405 alternately rises and falls during the alternate two phases of each cycle of transistors 235 and 236, respectively. This upward and downward voltage on capacitor 405 is translated into corresponding upward and downward currents from transistors 247 and 250.

Transistor 247 modulates the charging current for capacitor 403 which in turn determines the repetition frequency of the basic oscillator. Thus, transistor 247 and its associated circuitry essentially fulfills the function attributed to the frequency modulator 108 of the FIG. 1 embodiment. In FIG. 2A, transistor 250 similarly modulates the pulse duration of the basic oscillator by modulating the charging current of capacitor 404. This corresponds to the operation of the pulse duration modulator 109 of FIG. 1.

Since the current at the emitter of transistor 246 is nearly identical to the collector current of transistor 246, there occurs a similar alternating up and down current available from transistors 251 and 253, to that previously described. Transistors 251 and 253 provide currents to the output circuits in FIG. 2B, so that the amplitude of pulses from transistors 260 and 267, hereinafter described in greater detail, is similarly modulated. The emitter resistances in transistors 247, 250, 251, and 253 are selected so that the amount of scan or warbling is determined. That is, resistors 365,366,349,340,346,347, and 356 afford an opportunity for adjustability of the various pulse frequency, pulse width, and pulse amplitude modulation parameters.

In order to obtain the desired alternating output pulse polarity, or to obtain a dual output, there is need to break the oscillator output frequency into two parts. This is done by means of an alternating gate circuit shown in FIGS. 2A and 2B, which fulfills the functions attributed to alternating flip-flop 105 and output gate 106 of the embodiment of FIG. 1. In FIGS. 2A and 2B, an alternating gate is provided by a monostable multivibrator formed by transistors 216 and 219. Transistors 217 and 218 provide a steering input to cause the alternating gate to flip from one state to the other with each oscillator impulse. The collector voltage of transistor 219 is coupled via transistor 220, and in turn via transistors 260 and 267, to the respective transformers T1 and T2, and thus to the output terminals and the electrodes disposed on the patient's body.

Since the respective outputs are identical, the following discussion concerning production of stimulating pulses at the first output transformer T1 is to be understood to apply similarly with respect to the second output circuit via transformer T2. Transformer T1 has its primary winding connected to the collector of the output transistor 260. This configuration will be recognized as a current source output. Since the primary current in the transformer is relatively large, a large amount of gain is required between the output transistor and the control circuitry. This gain is provided by transistors 258 and 259. In the absence of any control, the current into the base of transistor 258 is determined by the potentiometer defined by resistor 346, in conjunction with a current limiting resistor 345. Normally, the base of transistor 258 is shorted to ground potential by transistor 212. When the basic oscillator is in its conducting phase, as hereinbefore described, transistor 212 is open circuited so that there is an output forthcoming from the transformer T1. Transistor 211 fulfills the same function with respect to the second output at transformer T2. The one of the outputs elicited is determined by which of the transistors 215 or 220 is conducting. If transistor 215 is conducting, then an output is obtained at transformer T1; whereas if transistor 220 is conducting, then the output is forthcoming from transformer T2.

A capacitor 409 is shown connected between the transistor 258 and ground, thereby providing a shut-off decay time of the output pulse. Capacitor 415 similarly controls rise time.

By alternating the output pulses from one output to the other, the patient is prevented from receiving the combined effect of two simultaneous outputs. Correspondingly, excessive demands on the battery are likewise prevented.

Protection circuitry is provided at transistors 254, 255, 256, and 257 for sensing discontinuity at the output, such as might eventuate if the electrodes are accidentally detached from the patient. In order to avoid discomfort or danger to the patient, this aspect of the circuitry of FIGS. 2A and 2B provides an automatic disconnect function. Diode DS1 provides an indication to the user of the exercise of this feature. This so-called "sentinel" feature attributed to block 111 of FIG. 1, is generally disclosed and claimed in two U.S. Patents owned by the assignee hereof, Nos. 4,068,669 and 4,088,141.

It is to be understood that the foregoing has set forth illustrative and preferred embodiments of the present invention, but that numerous alternative embodiments will occur to those of ordinary skill in the art without departure from the spirit or scope of the principles of the present invention.

What is claimed is:

1. A transcutaneous electrical nerve stimulator for pain control comprising:
   oscillator means for generating a stimulation control pulse signal having predetermined rate, pulse width, and pulse amplitude factors;

output means for producing nerve stimulating pulse signals having parameters as respective functions of said factors;

said output means comprising means for independently establishing and independently controlling the pulse rise time and pulse decay time of select pulses of said stimulating signal selectively to establish a stimulating signal waveshape to which given nerves are selectively responsive, thereby producing effective pain control with respect to said given nerves.

2. A stimulator as described in claim 1 and further comprising means, responsive to said oscillator means, for alternating the polarity of successive pulses of said control signal, and for coupling said pulses of alternating polarity to said output means, wherein said means for independently establishing separately to controls pulse rise times and fall times of positive going pulses in a first predetermined fashion, and to control pulse rise times and fall times of negative going pulses in a second predetermined fashion.

3. A stimulator as described in claim 2, wherein said output means further comprises means for establishing negative going pulses having peak amplitudes which are smaller than peak amplitudes of corresponding interleaved positive going pulses.

4. A stimulator as described in claim 3 wherein said exponential trailing edges are established havng a time constant in the range of 25 micro-seconds to 50 micro-seconds.

5. A stimulator as described in claim 1 wherein said means for independently establishing establishes an exponential amplitude versus time characteristic for the trailing edges of at least select pulses of the stimulation signal.

* * * * *

UNITED STATES PATENT AND TRADEMARK OFFICE
CERTIFICATE OF CORRECTION

PATENT NO. : 4,237,899

DATED : December 9, 1980

INVENTOR(S) : Norman R. Hagfors and John Walter Keller, Jr.

It is certified that error appears in the above-identified patent and that said Letters Patent are hereby corrected as shown below:

Column 9, line 7: "separately to controls" should be --separately controls--

Signed and Sealed this

Second Day of June 1981

[SEAL]

Attest:

RENE D. TEGTMEYER

Attesting Officer     Acting Commissioner of Patents and Trademarks